US010500102B2

(12) United States Patent
Duda

(10) Patent No.: US 10,500,102 B2
(45) Date of Patent: *Dec. 10, 2019

(54) SOCK FOR TREATMENT OF FOOT AND LEG WOUNDS, METHODS OF USE AND MANUFACTURE

(71) Applicant: Vive Wear LLC, Greensboro, NC (US)

(72) Inventor: Marcus Duda, Greensboro, NC (US)

(73) Assignee: Vive Wear LLC, Greensboro, NC (US)

( * ) Notice: Subject to any disclaimer, the term of this patent is extended or adjusted under 35 U.S.C. 154(b) by 732 days.

This patent is subject to a terminal disclaimer.

(21) Appl. No.: 14/976,931

(22) Filed: Dec. 21, 2015

(65) Prior Publication Data

US 2016/0136001 A1 May 19, 2016

Related U.S. Application Data

(63) Continuation of application No. 13/737,424, filed on Jan. 9, 2013, now Pat. No. 9,220,636.

(Continued)

(51) Int. Cl.
A61F 13/08 (2006.01)
A61F 13/00 (2006.01)
(Continued)

(52) U.S. Cl.
CPC .............. A61F 13/08 (2013.01); A41B 11/00 (2013.01); A41B 11/02 (2013.01); A41B 11/12 (2013.01);
(Continued)

(58) Field of Classification Search
CPC ... A41B 11/00; A41B 11/121; A41B 2400/60; A41B 2500/10; A41D 13/06; A61F 13/08; D04B 1/265
(Continued)

(56) References Cited

U.S. PATENT DOCUMENTS 4,206,514 A 6/1980 Yamauchi
4,852,453 A 8/1989 Morin
(Continued)

FOREIGN PATENT DOCUMENTS

WO WO 2008/007908 1/2008
WO WO 2013/106410 7/2013
WO WO 2014/057285 4/2014

OTHER PUBLICATIONS

Sukdeb et al. (Does the Antibacterial Activity of Silver Nanoparticles Depend on the Shape of the Nanoparticle? A Study of the Gram-Negative Bacterium *Escherichia coli*; Applied and Environmental Microbiology, Mar. 2007, p. 1712-1720).*

(Continued)

*Primary Examiner* — Ophelia A Hawthorne
*Assistant Examiner* — Caitlin A Carreiro

(57) ABSTRACT

The Improved Sock is made of yarns knitted to include a foot portion and a calf portion, with graduated compression on an individual's foot from the foot to the calf. The yarns can include wool and alpaca fibers. A substantial proportion of wool and/or alpaca are on the inside of the sock so as to be in direct contact with the skin and wound. The Improved Sock provides absorption and wicking of inflammatory mediators, bacteria and biofilm and necrotic exudate from the foot and leg. The Improved Sock has AgNP shapes electrostatically bonded to the yarn. At least 30% of the mass of the AgNP shapes attached to the fibers have a shape selected from the group including truncated triangular plates (a triangle with the corners rounded off), triangular prisms, and/or discs. The Improved Sock functions as a unique wound dressing with the sock in direct contact with the wound.

9 Claims, 3 Drawing Sheets

Related U.S. Application Data

(60) Provisional application No. 61/584,984, filed on Jan. 10, 2012.

(51) Int. Cl.

| | | |
|---|---|---|
| *D04B 1/26* | (2006.01) | |
| *D06B 1/00* | (2006.01) | |
| *A43B 17/00* | (2006.01) | |
| *A41D 13/00* | (2006.01) | |
| *A41D 13/05* | (2006.01) | |
| *A41B 11/00* | (2006.01) | |
| *A41B 11/14* | (2006.01) | |
| *A41B 11/12* | (2006.01) | |
| *A43B 13/00* | (2006.01) | |
| *A43B 17/14* | (2006.01) | |
| *A61F 13/06* | (2006.01) | |
| *D06M 11/83* | (2006.01) | |
| *D06M 16/00* | (2006.01) | |
| *D06M 23/08* | (2006.01) | |
| *A41B 11/02* | (2006.01) | |
| *A41D 13/06* | (2006.01) | |
| *D06M 101/12* | (2006.01) | |

(52) U.S. Cl.
CPC ............ *A41B 11/121* (2013.01); *A41B 11/14* (2013.01); *A41D 13/00* (2013.01); *A41D 13/05* (2013.01); *A41D 13/06* (2013.01); *A43B 13/00* (2013.01); *A43B 17/00* (2013.01); *A43B 17/14* (2013.01); *A61F 13/00012* (2013.01); *A61F 13/00042* (2013.01); *A61F 13/06* (2013.01); *D04B 1/265* (2013.01); *D06B 1/00* (2013.01); *D06M 11/83* (2013.01); *D06M 16/00* (2013.01); *D06M 23/08* (2013.01); *A41B 2400/34* (2013.01); *A41B 2400/60* (2013.01); *A41B 2500/10* (2013.01); *D06M 2101/12* (2013.01)

(58) Field of Classification Search
USPC .......................................... 602/44
See application file for complete search history.

(56) References Cited

U.S. PATENT DOCUMENTS

| | | | |
|---|---|---|---|
| 5,458,906 | A | 10/1995 | Liang |
| 5,496,860 | A | 3/1996 | Matsumoto et al. |
| 5,898,948 | A | 5/1999 | Kelly et al. |
| 6,124,221 | A | 9/2000 | Gabbay |
| 6,522,918 | B1 | 2/2003 | Crisp et al. |
| 6,946,196 | B2 | 9/2005 | Foss |
| 6,979,491 | B2 | 12/2005 | Yan et al. |
| 7,007,517 | B2 | 3/2006 | Menzies |
| 7,213,420 | B2 | 5/2007 | Lynch et al. |
| 7,441,419 | B1* | 10/2008 | Dollyhite ................ A61F 13/08 66/178 A |
| 7,552,603 | B2 | 6/2009 | Dahlgren |
| 7,662,176 | B2 | 2/2010 | Skiba et al. |
| 7,950,071 | B2 | 5/2011 | Jeong |
| 8,075,507 | B2 | 12/2011 | Linnane et al. |
| 9,220,636 | B2* | 12/2015 | Duda ..................... D06M 16/00 |
| 9,387,125 | B1 | 7/2016 | Duda |
| 2003/0176827 | A1 | 9/2003 | Chandra et al. |
| 2003/0190851 | A1 | 10/2003 | Yan et al. |
| 2004/0267237 | A1 | 12/2004 | Sun et al. |
| 2006/0010574 | A1 | 1/2006 | Linnane et al. |
| 2006/0253078 | A1 | 11/2006 | Wu et al. |
| 2006/0264796 | A1 | 11/2006 | Flick et al. |
| 2007/0088341 | A1 | 4/2007 | Skiba et al. |
| 2007/0207335 | A1* | 9/2007 | Karandikar ............. C09D 7/67 428/560 |
| 2007/0283483 | A1 | 12/2007 | Jacober |
| 2007/0293800 | A1 | 12/2007 | McMaken et al. |
| 2008/0071204 | A1 | 3/2008 | Linnane et al. |
| 2008/0249454 | A1* | 10/2008 | Mills ....................... A61F 13/08 602/63 |
| 2009/0025359 | A1 | 1/2009 | Chandra et al. |
| 2009/0035342 | A1 | 2/2009 | Karandikar et al. |
| 2009/0280151 | A1 | 11/2009 | Restani et al. |
| 2010/0069813 | A1 | 3/2010 | Crisp |
| 2010/0137776 | A1 | 6/2010 | Virkus et al. |
| 2011/0236343 | A1 | 9/2011 | Chisholm et al. |
| 2013/0178779 | A1 | 7/2013 | Duda |
| 2014/0276275 | A1 | 9/2014 | Stokes et al. |
| 2015/0157524 | A1 | 6/2015 | Reid, Jr. et al. |
| 2017/0209683 | A1 | 7/2017 | Duda |

OTHER PUBLICATIONS

Sun et al. (Triangular Nanoplates of Silver: Synthesis, Characterization, and Use as Sacrificial Templates for Generating Triangular Nanorings of Gold: Adv. Mater. 2003, 15, No. 9, May 2—pp. 695-699).*

Office Action for U.S. Appl. No. 13/737,424, dated Feb. 20, 2015, 9 pages.

International Search Report and Written Opinion for International Application No. PCT/US2013/020803, dated Jun. 27, 2013, 7 pages.

Abbade, L. P. F. et al., "Venous ulcer: epidemiology, physiopathology, diagnosis and treatment," Int. J. Dermatology, 44(6):449-456 (Jun. 2005).

Atiyeh, B. S. et al., "Effect of silver on burn wound infection control and healing: Review of the literature," Burns, 33(2):139-147 (2007).

Benn, T. M. et al., "Nanoparticle silver released into water from commercially available sock fabrics," Environ. Sci. Technol, 42(11):4133-4139 (Jun. 2008).

Braun, L. et al., "What's new in the literature: An update of new research since the original WHS diabetic foot ulcer guidelines in 2006," Wound Repair and Regeneration 22(5):594-604 (2014).

Cupron, Inc., "About Cupron," Cupron Enhanced, 2008, 6 pages.

Finley, P. J. et al., "Silver dressings improve diabetic wound healing without reducing bioburden," Wounds, 25(10):293-301 (2013).

Gabriel, A. et al. "Reducing bacterial bioburden in infected wounds with vacuum assisted closure and a new silver dressing—a pilot study." Wounds—A Compendium of Clinical Research and Practice 18(9) (2006): 245-255.

Gardner, S. E. et al. "Effect of electrical stimulation on chronic wound healing: a meta-analysis." Wound Repair and Regeneration, 7(6):495-503 (1999).

Garduque, Gian et al. "Silver as an Antimicrobial Agent—MicrobeWiki." Silver as an Antimicrobial Agent. MicrobeWiki, 2010. Web. Retrieved Feb. 24, 2016. <http://microbewiki.kenyon.edu/index.php/Silver_as_an_Antimicrobial_Agent.

Hatchett, D. W. et al., "Electrochemistry of sulfur adlayers on the low-index faces of silver," The Journal of Physical Chemistry, 100(23):9854-9859 (1996).

Herber, O. R. et al., "A systematic review on the impact of leg ulceration on patients' quality of life," Health and Quality of Life Outcomes, 5:44 (Jul. 2007), Published online Jul. 25, 2007.

Impellitteri, C. A. et al., "The speciation of silver nanoparticles in antimicrobial fabric before and after exposure to a hypochlorite/detergent solution," Journal of Environmental Quality, 38:1528-1530 (2009).

Johannes, L., "Silver lining to fighting germs," The Wall Street Journal [online], Jul. 19, 2011, 3 pages.

Kelly, F. M. et al., "Functionalised hybrid materials of conducting polymers with individual wool fibers," Journal of Nanoscience and Nanotechnology, 8(4):1965-1972 (2008).

Kirsner, R. S. et al., "Matrix metalloproteinases in normal and impaired wound healing: a potential role of nanocrystalline silver," Wounds, 13:4-12 (2002).

Ladwig, G. P. et al., "Ratios of activated matrix metalloproteinase-9 to tissue inhibitor of matrix metalloproteinase-1 in would fluids are inversely correlated with healing of pressure ulcers," Wound Repair and Regeneration, 10(1):26-37 (Jan. 2002).

(56) References Cited

OTHER PUBLICATIONS

Liu, X. et al., "Resistance to compression behavior of alpaca and wool," Textile Research Journal, 74(3):265-270 (2004).

Liu, Y. et al., "Increased matrix metalloproteinase-9 predicts poor wound healing in diabetic foot ulcers," Diabetes Care, 32(1):117-119 (Jan. 2009).

Longo, A. et al., "Dependence of optical and microstructure properties of thiol-capped silver nanoparticles embedded in polymeric matrix," Polymers, 3(4):1794-1804 (2011).

McCarty, S. M. et al., "The role of endogenous and exogenous enzymes in chronic wounds: A focus on the implications of aberrant levels of both host and bacterial proteases in wound healing," Wound Repair and Regeneration, 20(2):125-136 (2012).

Nair, L. S. et al., "Silver nanoparticles: Synthesis and therapeutic applications," Journal of Biomedical Nanotechnology, 3(4):301-316 (2007).

Pal, S. et al., "Does the antibacterial activity of silver nanoparticles depend on the shape of the nanoparticle? A study of the gram-negative bacterium escgerichia coli," Applied and Environmental Microbiology, 73(6):1712-1720 (Mar. 2007).

Palfreyman, S. J. et al., "Dressings for healing venous leg ulcers," Chochrane Database Syst. Rev., (3):CD001103 (Jul. 2006).

Percival, S. L. et al., "Assessing the effect of an antimicrobial wound dressing on biofilms." Wound Repair and Regeneration, 16(1):52-57 (2008).

Percival, S. L. et al., "Antimicrobial activity of silver-containing dressings on wound microorganisms using an in vitro biofilm model,", Int. Wound J., 4(2):186-191 (2007).

Pfurtscheller, K. et al., "Transdermal uptake and organ distribution of silver from two different wound dressings in rats after a burn trauma," Wound Repair and Regeneration, 22(5):654-659 (2014).

Prakash, S. et al. "Venous Ulcer: Review Article" Surgical Science, 2013, 4, 144-150.

Rayment, E. A. et al., "Increased matrix metalloproteinase-9 (MMP-9) activity observe in chronic wound fluid is related to the clinical severity of the ulcer," Br. J. Dermatol., 158(5):951-961 (May 2008).

Reiss, M. J. et al., "α1-Antichymotrypsin activity correlates with and may modulate matrix metalloproteinase-9 in human acute wounds," Wound Repair and Regeneration, 17(3):418-426 (May/Jun. 2009).

Sun, R. W. et al., "Silver nanoparticles fabricated in Hepes buffer exhibit cytoprotective activities toward HIV-1 infected cells," Chem. Commun. (Camb.), 40:5059-5061 (2005).

Tang, B. et al., "Application of anisotropic silver nanoparticles: Multifunctionalization of wool fabric," Journal of Colloid and Interface Science, 356(2):513-518 (2011).

Tian, J. et al., "Topical delivery of silver nanoparticles promotes wound healing," ChemMedChem., 2(1):129-136 (Jan. 2007).

Trengove, N. J. et al., "Analysis of the acute and chronic would environments: the role of proteases and their inhibitors," Wound Repair and Regeneration, 7(6):442-452 (1999).

Trial, C. et al., "Assessment of the antimicrobial effectiveness of a new silver alginate wound dressing: a RCT," Journal of Wound Care, 19(1):20-26 (Jan. 2010).

Valencia, I. C. et al., "Chronic venous insufficiency and venous leg ulceration," Journal of the American Academy of Dermatology, 44(3):401-421 (Mar. 2001).

Varner, K. et al., "State of the Science Literature Review: Everything Nanosilver and More," Scientific, Technical, Research, Engineering and Modeling Support Final Report, Contract No. EP-C-05-057, Task Order No. 95, U.S. Environmental Protection Agency, (Aug. 2010), 221 pages.

Widgerow, A. D., "Nanocrystalline silver, gelatinases and the clinical implications," Burns, 36(7):965-974 (2010).

Wijnhoven, S. W. P. et al., "Nano-silver—a review of available data and knowledge gaps in human and environmental risk assessment," Nanotoxicology, 3(2):109-138 (Jun. 2009).

Wong, K. K. Y. et al., "Further evidence of the anti-inflammatory effects of silver nanoparticles," ChemMedChem., 4:1129-1135 (2009).

Wright, J. B. et al., "Early healing events in a porcine model of contaminated wounds: effects of nanocrystalline silver on matrix metalloproteinases, cell apoptosis, and healing," Wound Repair Regen., 10(3):141-151 (2002).

Wright, J. B. et al., "Wound management in an era of increasing bacterial antibiotic resistance: A role for topical silver treatment," American Journal of Infection Control, 26(6):572-577 (Dec. 1998).

Wright, J. B. et al., "Efficacy of topical silver against fungal burn wound pathogens," Am. J. Infect. Control, 27(4):344-350 (Aug. 1999).

Yager, D. R., "Wound fluids: A window into the wound environment?", The International Journal of Lower Extremity Wounds, 6(4):262-272 (Dec. 2007).

Yager, D. R. et al., "Wound fluids from human pressure ulcers contain elevated matrix metalloproteinase levels and activity compared to surgical wound fluids," J. Invest. Dermatol., 107(5):743-748 (1996).

Office Action for U.S. Appl. No. 15/006,781, dated Apr. 21, 2016, 13 pages.

Office Action for U.S. Appl. No. 15/205,826, dated Nov. 28, 2018, 16 pages.

International Search Report and Written Opinion for International Application No. PCT/US2017/015106, dated May 4, 2017, 9 pages.

Ornes, S., "'Smart' clothes generate electricity. New fabric harvests energy from its wearer," Technology & Engineering, Physics, [online], Mar. 23, 2015, 4 pages. Retrieved from the Internet: <URL: https://student.societyforscience.org/article/%E2%80%98smart%E2%80%99-clothes-generate-electricity>.

* cited by examiner

SOCK FOR TREATMENT OF FOOT AND LEG WOUNDS, METHODS OF USE AND MANUFACTURE

This application is a continuation of U.S. patent application Ser. No. 13/737,424, entitled "Sock For Treatment of Foot and Leg Wounds, Methods of Use and Manufacture," filed Jan. 9, 2013 (now U.S. Pat. No. 9,220,636), which claims priority to, and the benefit of Provisional Application Ser. No. 61/584,984, entitled "Sock For Treatment of Foot and Leg Wounds, Methods of Use and Manufacture," filed Jan. 10, 2012, which is incorporated herein by reference in its entirety.

BACKGROUND OF THE INVENTION

Leg ulceration is the most prevalent chronic wound in Western countries, affecting about 1 to 2% of the adult population (Valencia I C, Falabella A, Kirsner R S, Eaglstein W H. Chronic venous insufficiency and venous leg ulceration. J Am Acad Dermatol 2001; 44: 401-21). The main causes of leg ulceration are venous hypertension, arterial insufficiency, and diabetes. Venous ulcers account for approximately 80% of all leg ulcers and are the result of venous hypertension. The current treatment for venous ulcers includes graduated compression support stockings or compression bandaging of the limb Despite the standard of care of compression therapy, 50 to 70% of venous leg ulcers remain unhealed after 12 weeks of treatment and 54 to 78% of ulcers will reoccur (Abbade L P, Lastoria S. Venous ulcer:epidemiology, physiopathology, diagnosis and treatment. Int Wound J 2006; 3:113-20). These chronic wounds have a treatment cost in the United States of approximately one billion dollars per year and have a significant impact on the patient's quality of life (Herber O R, Schnepp W, Rieger M A. A systemic review on the impact of leg ulceration on patient's quality of life. Health Qual Life Outcomes 2007; 5: 44).

The biology of the chronic venous and diabetic wounds is quite different from acute wounds. In an acute wound the initial fibrin clot provides hemostasis and the platelets release cytokines, growth factors, and recruit inflammatory cells. The recruitment of inflammatory cells includes neutrophils and macrophages to eradicate bacteria. At the leading edge of the wound the protease cut through the fibrin clot. Matrix Metalloproteinases (MMP) are up regulated by the keratinocyte to cut a path through the matrix proteins to allow the keratinocyte to advance and close the wound. MMP-9 (gelatinase B) cuts through the basal lamina collagen (type IV) and anchoring collagen (type VII) to allow the keratinocytes to advance and close the wound. Once the keratinocytes cover the wound, the wound is re-epithelized, the basal lamina is reestablished and the MMP-9 is shut off.

However, in a chronic wound, the MMP-9 is not shut off. The elevated levels of this protease continue to destroy the wound matrix that is produced to heal the wound. The level of MMP-9 in a chronic wound can be five times of its level in an acute wound (Yager et al, 1996, Trengove et al, 1999). MMP-9 is the major protease that is present in the chronic venous stasis and decubitus ulcers.

The tissue inhibitor of metalloproteinase (TIMP-1) is absent from chronic wounds and is also decreased with age.

These chronic wounds also become colonized with bacteria. The bacterial colonies produce a biofilm which enables the bacteria to act as a multicellular organism. The biofilm protects the bacteria from the host immune system and all antibiotics. The bacterial biofilm gains nutrients from its own protease, which are similar to the host MMP-9. The biofilm then protects the bacteria from the host immune system and all antibiotics.

Thus, in chronic wounds, the bacterial biofilm and the host both produce proteases which are responsible for the degradation of the factors responsible for wound healing.

Current wound care products, including silver ointments and dressings, show no improvement in the healing rates of chronic venous or diabetic ulcers when used with compression therapy. (Palfreyman S, Nelson E A, Michaels J A. Dressings for venous leg ulcers: systemic review and meta-analysis. BMJ 2007; 335: 244).

There is a need to develop a new wound care treatment for chronic wounds that would decrease the socioeconomic impact of wound care and would improve healing rates.

The innovative proposed Improved Sock is comprised of a combination of silver nanoparticle (AgNP) shapes, natural wicking fibers, and elastic fibers composed into a yarn knitted to make the sock. The sock is applied directly on the wound with the natural wicking fibers with adhered AgNP shapes coming into contact with the wound. The Improved Sock directly down regulates the MMP-9 and bacterial proteases, kills the bacteria that is protected by the biofilm, and allows the epithelialization of the wound without harming the keratinocytes. The preferred natural wicking fibers are wool, such as merino wool, and/or alpaca.

Medical compression socks are known to increase the circulation in the feet and legs. The use of silver nanoparticles has proven to have antibacterial, antifungal and antiviral properties.

Currently, AgNPs have been used on textiles such as socks, clothing, and wound dressings. The AgNPs are either coated on the wound dressing or textile or they are incorporated into a polyester yarn, which is knitted with other fibers to create socks, clothing or wound dressing.

Current research shows that the AgNPs can be manufactured into specific shapes which show improved antibacterial properties (Pal, S., Y. K. Tak and J. M. Song, 2007, Does the antibacterial activity of silver nanoparticles depend on the shape of the nanoparticle? A study of the gram-negative bacterium Escherichia coli. Appl. Environ. Microbiol. 2007, 73(6):1712). The AgNP shapes also demonstrate improved anti-inflammatory and angiogenic properties. The specific AgNP shapes which have shown improved antibacterial, anti-inflammatory, and angiogenic properties include silver nano prisms (AgNPr), silver nano truncated triangle plates (AgNTTP), and silver nano discs (AgND). Currently, a commercial product does not exist that combines the features of manufactured AgNP shapes (AgNPr, AgNTTP, AgND) with a compression sock made of natural fiber. The AgNP shapes allow for the use of a lower concentration of silver and results in a more effective wound care treatment. This new innovation will uniquely address the needs of patients with chronic wounds. The Improved Sock will increase circulation and will decrease the bacterial, fungal and viral loads that cause infections. This Improved Sock will also decrease the chronic inflammatory mediators which prevent wound healing and will stimulate wound healing by angiogenesis.

SUMMARY

The present invention fulfills one or more of these needs in the art by providing a sock made of yarns knitted with graded compression on the individual from the foot to below the knee. The yarns, including wool and alpaca fibers, will be a substantial proportion of the inside of the sock, so as to be in direct contact with the skin and wound. The Improved Sock provides cushion, absorption and wicking of exudate and necrotic tissue from the leg and foot. In one embodiment, AgNP shapes (AgNPr, AgNTTP, AgND) are located on the yarn and manufactured from AgNPs wherein at least 30% of the mass of the AgNPs attached to the fibers have a AgNPr, AgNTTP or AgND shape. In another embodiment, the manufactured AgNP shapes (AgNPr, AgNTTP, AgND) are combined in a ratio to maximize the anti-bacterial, anti-inflammatory, and angiogenic properties. In an embodiment, the mass of the AgNP shapes is less than 0.1% of the weight of the total weight of the sock.

The invention is considered a unique method of wound treatment. A patient's donning of the sock and placement directly on the wound can easily and efficiently provide wound care without the expense and time of multiple wound care products and the associated doctor and nursing care visits. In one embodiment, the yarns of the sock include at least one of wool and alpaca fibers and a substantial proportion of the inside of a sock is wool and alpaca fibers so as to be in contact with the skin and provide absorption and wicking of bacteria, inflammatory exudate, and necrotic tissue from the leg and foot. The yarns made of wool and alpaca fibers can be knitted into a terry pattern over high stress areas that are at risk of insensate neuropathic ulcers. AgNP shapes are selected from the AgNPr, AgNTTP, and AgND.

In one embodiment of the invention, AgNP shapes are bound to the wool and alpaca fibers through electrostatic forces. The first act is to make an aqueous suspension including the AgNP shapes. The wool and alpaca fibers are then exposed to the aqueous solution. The aqueous solution pH is decreased and temperature increased to maximize the electrostatic force of the bond between the wool, alpaca, and the AgNP shapes.

The invention is considered a wearable wound dressing that can also prevent bacterial and fungal infections of the lower extremity. The ease of use, comfort, and low maintenance of the sock makes it ideal for patient compliance. The wearable wound dressing minimizes the labor and material expense required to provide wound care dressing changes by health care professionals.

BRIEF DESCRIPTION OF THE DRAWINGS

The invention will be better understood by reading the Detailed Description of the Examples of the Invention along with a review of the drawings in which.

DETAILED DESCRIPTION OF EXAMPLES OF THE INVENTION

Figure 1:
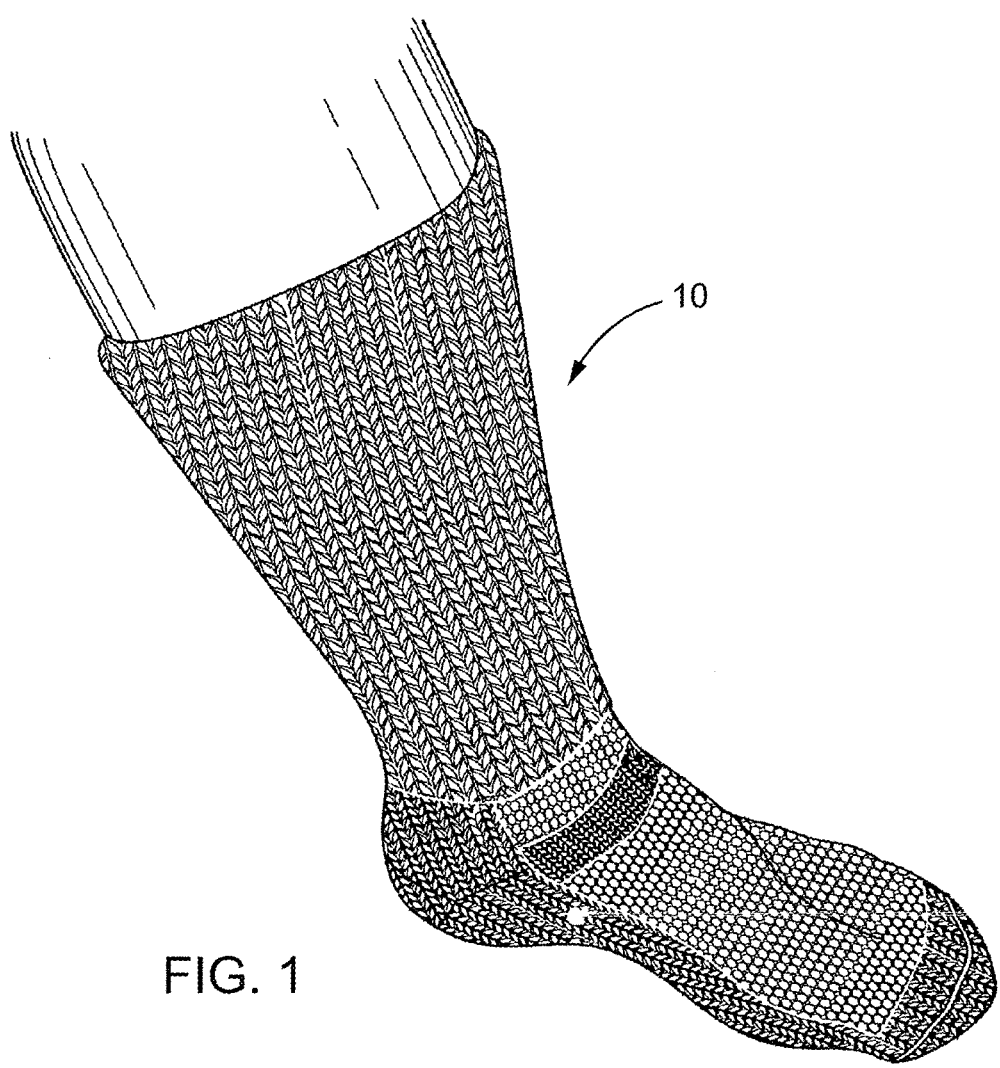
FIG. 1 is a view of a sock in accordance with the invention.

The Improved Sock (as seen in FIG. 1) is used particularly for patients with ulcerations from arterial, venous and lymphatic insufficiency, diabetes, and for other people as well. It has graduated compression from the foot up through the calf. Thus, the sock includes characteristics of graduated compression, the presence of anti-microbial, anti-inflammatory, and angiogenic AgNP shapes, and the wool and alpaca fibers. The wool and alpaca is in contact with the skin and provides pleasing comfort and durability to the wearer. The wool and alpaca yarns are knitted into a terry pattern over high stress areas such as the tibial crest, the heel and forefoot. To maintain equal compression around the ankle malleoli, the terry is strategically placed to cradle the medial and lateral malleoli.

The sock is knitted from a yarn that has both a wool and/or alpaca component and an elastic component. A currently preferred yarn is a 50/50 blend of alpaca and merino wool, with the merino and alpaca fibers about 18.5 microns in diameter, spun into a yarn with dimensions of 1/44 NM (single yarn, 44 number metric in diameter). Various wools can be used, but merino wool is presently preferred. The wool and/or alpaca is placed in the yarn in a covering arrangement so it, not the elastic, is in contact with the skin and wound. Thus, the elastic forms the core of the yarn. Various elastic yarns can be used. Double covered elastic yarns are currently preferred in order to achieve the degree of compression disclosed herein. Other materials may be suitable for the elastic fibers, such as latex or latex-free elastomers, spandex, various rubbers, texturized polyester and/or nylon. As used in this context, "fibers" includes filament yarns.

The yarn is knit with a terry effect to get more of the merino (or other wool) and alpaca and silver shapes in contact within the depth of the wound.

The sock has graduated compression of 18-24 mm Hg. The higher compression starts in the foot and gradually decreases up the calf to decrease edema and increase circulation. Studies of compression in this range show increased circulation up to 40% and this compression is below the range that inhibits microcirculation in the skin.

The sock is knitted to obtain graduated compression and uses yarns of wool and alpaca fiber, with the addition of polyester and/or nylon. The alpaca fiber has a better wicking ability than wool, has better compressibility (provides more cushion), is softer, and more durable than wool (Liu, Xin, Wang, Lijing and Wang, Xungai, 2004, Resistance to compression behavior of alpaca and wool, Textile Research Journal, vol. 74, no. 3 pp. 265-270). The wool and alpaca are able to wick away the inflammatory exudate, the bacteria and biofilm, and debride necrotic tissue from the wound while maintaining a moist wound environment.

Figure 2A:
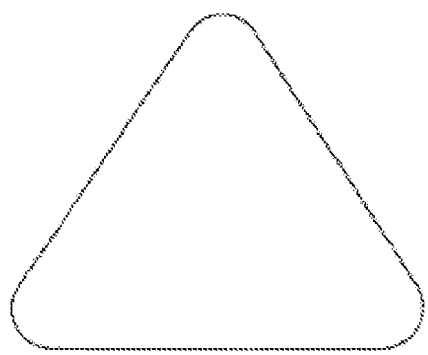
FIGS. 2A-2C are views of example shapes of a silver nanoparticle to be adhered to or included in the yarn of the sock, including a truncated triangular plate (AgNTTP) (FIG. 2A), a triangular prism (AgNTP) (FIG. 2B), and a disc (AgND) (FIG. 2C)
Figure 2B:
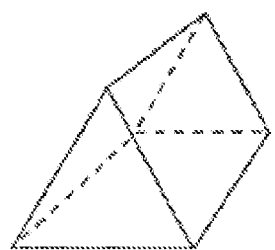
Figure 2C:
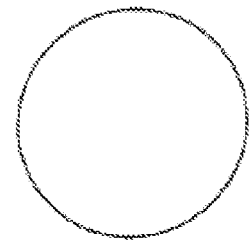

In one embodiment, the AgNP shapes attached to the fibers have at least 30% of the mass of the AgNPs in a shape where the length of the two principal axes of the nanoparticle are more than three times greater than the length of the third principal axis of the nanoparticle and where the length of the third principal axis is less than 50 nm (FIG. 2A and FIG. 2C). In another embodiment, the AgNP shapes have a triangular prism shape (FIG. 2B). The AgNP shapes can include mixtures of two or more of the different types of shapes. The truncated triangular silver nano plates have shown the strongest antibacterial activity due to the surface {111} facet characteristics (Wijnhoven, S. W. P., Peijnenburg, Willie J. G. M., Herberts, Carla A., Hagens, Werner I., Oomen, Agnes G., Heugens, Evelyn H. W., Roszek, Boris, Bisschops, Julia, Gosens, Ilse, Van De Meent, Dik, Dekkers, Susan, De Jong, Wim H., van Zijverden, Maaike, Sips, Adrienne J. A. M. and Geertsma, Robert E., 2009. Nanosilver—a review of available data and knowledge gaps in human and environmental risk assessment. Nanotoxicology, 3:2, 109-138). The reactivity of the nano silver is improved by the high atom density surface { 111} facet (Hatchett, D.

W. and Henry, S. 1996, Electrochemistry of sulfur adlayers on low-index faces of silver. Jl. Phys. Chem. 100:9854-9859).

The silver nanoparticles also demonstrate strong anti-fungal properties (Wright, J. B., Lam K, Hansen D., Burrell R. E., 1999, Efficacy of topical silver against fungal burn wound pathogens. Am. Jl. Infect. Control 27:344-350), anti-viral properties that inhibit HIV-1 replication (Sun, R. W., Chen R., Chung N. P., Ho C. M., Lin C. L., Che C. M. 2005. Silver nanoparticles fabricated in Hepes buffer exhibit cyto-protective activities toward HIV-1 infected cells. Chem. Commun (Camb.):5059-5061), and anti-inflammatory properties (Kirsner R. S., Orsted H., Wrught J. B. 2002. Matrix metalloproteinases in normal and impaired wound healing: a potential role of nanocrystalline silver. Wounds 13:4-12).

Elevated inflammatory mediators are responsible for chronic wounds not healing The chronic inflammatory mediators that are most responsible for non-healing diabetic wounds include matrix metallo-proteinases (specifically MMP-9), tumor necrosis factor (TNF-alpha), and interluken (IL-1 and 12). (Rayment, E. A., Upton Z., Shooter G. K., 2008, Increased matrix metalloproteinase-9 (MMP-9) activity observed in chronic wound fluid is related to the clinical severity of the ulcer. British Jl. of Derm. 158, pp 951-961). The AgNP shapes with {111} facets that are used in the Improved Socks will suppress these proteolytic enzymes that are responsible for the non-healing chronic wounds (Wright J. B., Lam K., Buret A. G., Olson M. E., Burrell R. E., 2002, Early healing events in a porcine model of contaminated wounds: Effects of nanocrystalline silver on matrix metalloproteinases, cell apoptosis, and healing. Wound Repair Regen. 10:141-151).

The AgNP shapes can be added to the Improved Sock in a way that will be durable and machine washable. By placing the AgNP shapes in an acidic suspension (by decreasing the pH of the silver solution) it allows the silver nanoparticles to electrostatically bond to the wool fiber. AgNP shapes as described are reduced to the specified AgNP shapes through a reduction chemical reaction. With the electrostatic potential of the wool positive and the electrostatic potential of the silver negative, a strong and durable electrostatic bond is created (Tang, B., J Wang, S. Xu, T Afrin, W. Xu, L. Sun, X. Wang, 2011, Application of anisotropic silver nanoparticles: multi-funtionalization of wool fabric. J. of Colloid and Interface Science 356 (2011) 513-518). The AgNP shapes may also be bonded to a synthetic fiber which, when knitted with the wool and alpaca fibers, will provide the same function.

The AgNP shapes can become part of the sock in numerous ways. The silver solution can be sprayed onto the knitted sock to get an even distribution. The silver binds to the fiber rapidly so that soaking the sock in the silver solution risks a result that is not evenly distributed. It is believed that the silver can be applied to the yarn before knitting into the sock if the other finishing treatments are not too harsh.

Figure 3:
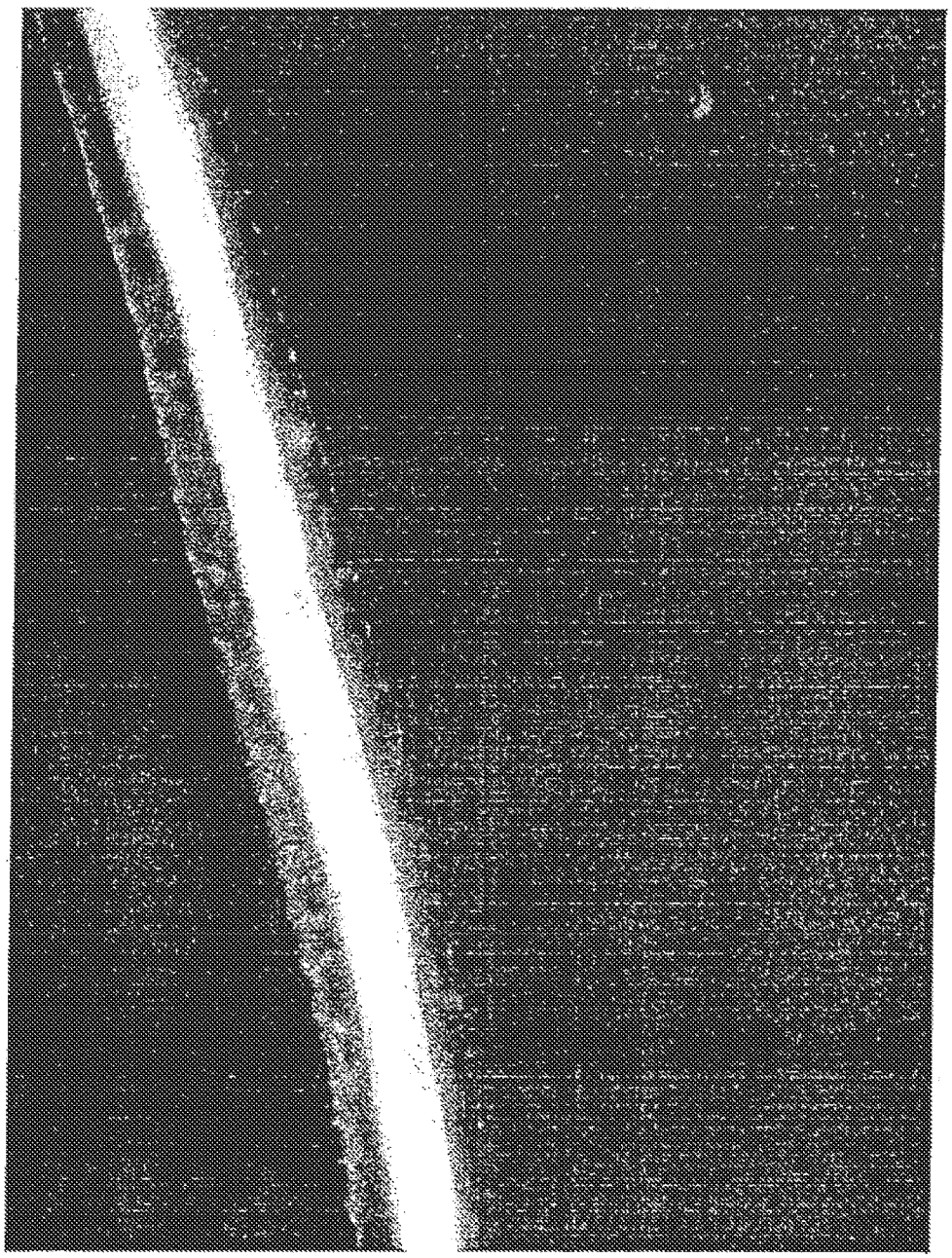
FIG. 3 is a photographic image of the silver plates bound to a sock fiber taken with dark field microscopy.

The strong bond of the AgNP shapes to the wool and alpaca fibers of the Improved Sock can be seen on microscopic images. FIG. 3 shows an image of a fiber removed from the Improved Sock that was treated with the AgNP shapes. This figure shows a dark field microscopic image of a fiber that has been placed in a refractive index matching oil. Dark field microscopy shows up scattered and reflected light. One of the things that show up well in dark fields are regions of different refractive index, as well as the silver plates, which show up as bright spots. In this case, the outer sheath of the wool fiber matches the refractive index of the oil, so it is transparent, while the inner portion of the fiber has a different refractive index so it shows up as a bright line. The AgNP shapes show up as bright spots along the edge of the fiber. They appear to trace the junctions of the scales on the outside of the fiber.

Chronic venous, lymphatic and diabetic wounds include a high bacterial load, glycoprotein biofilm, and chronic inflammatory mediators. The biofilm produced by the bacteria prevents the effectiveness of antibiotics and the host immune system against the bacteria. However, the AgNP shapes in the Improved Sock will inhibit the bacteria as well as the formation of the biofilm (Percival, S. L., Bowler P. G., Dolman J., 2007, Antimicrobial activity of silver-containing dressings on wound microorganisms using an in vitro biofilm model. Int. Wound Jl. 4:186-191).

The chronic inflammatory mediators of venous, lymphatic and diabetic wounds have been shown to play a major role in the prevention of wound healing. The chronic inflammatory mediator primarily responsible for the non-healing wounds is matrix metallo-proteinase 9 (MMP-9). The specific AgNP shapes chosen for the Improved Sock have been shown to be most effective in reducing MMP-9.

Embodiments of the Improved Sock improve circulation, decrease edema, decrease infection and improve wound healing by decreasing the biofilm burden and decreasing MMP-9.

Preliminary Clinical Trial

The preliminary clinical trial results of the Improved Sock are encouraging. Patients that had failed current standard of care treatment for lower extremity wounds were referred to a wound clinic for evaluation and treatment. After informed consent was obtained, six patients were started in a preliminary clinical trial using the Improved Sock with wool and alpaca fibers, elastic fibers for compression, and AgNP shapes (See Table 1). The age of these six preliminary clinical trial patients with chronic wounds (five patients) and acute wounds (one patient) ranged from 58 to 87.

TABLE 1

| Patient Age | Co-morbidities | Wound Duration (Months) | Wound Culture | Previous Antibiotic Treatment | Previous compression therapy | Wound size Cm$^2$ | Time to heal (weeks) | Sock changed worn 24/hr/day |
|---|---|---|---|---|---|---|---|---|
| 70 | HL,TR, CS | >12 | | | Mag | 50 | 12 | Weekly |
| 79 | EM,SM, HTN | 3 | | | SC,AC | 40 | 3 | Weekly |
| 24 | | 4 | MRSA | Clindamycin, Ciprofloxacin TMP-SMZ | | 1 | 1 | Weekly |
| 58 | DM,HTN,C | >12 | | Doxycycline, | SC,XC,SI | Entire | 10 | Daily |

TABLE 1-continued

| Patient Age | Co-morbidities | Wound Duration (Months) | Wound Culture | Previous Antibiotic Treatment | Previous compression therapy | Wound size $Cm^2$ | Time to heal (weeks) | Sock changed worn 24/hr/day |
|---|---|---|---|---|---|---|---|---|
| | O,LY, SA | | | Vancomycin Zosyn | | leg | | |
| 87 | SS, VSI, ARF | Acute | MRSA | Doxycycline | | Entire leg | 14 | Daily |

Abbreviations used in table:
COMORBIDITIES: ARF—acute renal failure; CO—COPD; DM—diabetes; EM—emphysema; HL—hyperlipidemia; HTN—hypertension; LY—lymphedema; SA—sleep apnea; SM—smoker; SS—septic shock; TR—trauma; VSI—venous stasis insufficiency
PREVIOUS COMPRESSION THERAPY: AC—ACell MatriStem®; CS—Kendal T.E.D.® hose; DY—Johnson and Johnson DYNA FLEX®; Mag—Molnlycke Mepilex® Ag; SC—Johnson and Johnson Silvercelle; SI—Silver sulfadiazine; UN—Unna boot; VAC—KCI wound V.A.C.® In all cases, the pain decreased. The only complication occurred in the 58 year old patient, whose wound healed uneventfully, despite a dorsal ankle ulcer from sock fold.

The chronic wound patients' previous treatment had included compression therapy using Kendal T.E.D compression stockings, Johnson and Johnson Dyna Flex compression wraps, and UNNA compression boot. One patient had a wound treated with a KCI wound V.A.C. Wound dressings included silver alginate such as Johnson and Johnson Silvercell, and Molnlycke Mepilex Ag. Treatment with skin graft substitutes included A-Cell, MatriStem, and Organogenesis, Apligraf. Prior therapies for the chronic wound patients enrolled in the preliminary clinical trial included several months of a broad spectrum of oral and intravenous antibiotics.

Despite aggressive standard of care treatment, all of the patients' wounds that were enrolled in the preliminary clinical trial of the Improved Sock, had failed to heal. Some of the chronic wounds treated with the Improved Sock had been present for several years.

As expected, the larger chronic wounds took longer to heal. Nonetheless, all of the wounds that had been present for over one year and then treated with the Improved Sock healed in 10 to 12 weeks, and have not recurred.

The one acute preliminary clinical trial patient with acute fungal and MRSA wounds healed in 2 weeks.

The most remarkable result using the Improved Sock occurred in an 87 year old woman who presented to the hospital in septic shock with circumferential ulceration of her left leg from the knee to ankle She had chronic venous stasis ulcers that failed treatment using compressive wrap with an UNNA boot. Her initial wound cultures were positive for MRSA. Initial consultation from a general surgeon was to consider an amputation of the leg above the knee. After informed consent with the patient and her family (including a dermatologist), they elected to try the Improved Sock. The Improved Sock was changed daily at bedside and washed in regular soap and water. The patient underwent no anesthesia or surgical debridements. After a week of rapid improvement the patient was discharged to a skilled nursing facility. While at the skilled nursing facility the wound care nurse resumed traditional wound dressing including graduated compression. After 2 weeks the wound became significantly worse. The Improved Sock was then reapplied and changed every 2 to 3 days depending on the amount of drainage. After 14 weeks the treated leg wounds completely healed. The patient is currently wearing the improved sock daily without any swelling or sign of skin breakdown. No ulcers have reoccurred two months after healing.

Certain modifications and improvements will occur to those skilled in the art upon reading the foregoing description. It should be understood that all such modifications and improvements have been omitted for the sake of conciseness and readability, but are properly within the scope of the following claims.

What is claimed is:

1. A sock for a patient with a wound on the patient's foot, ankle or calf comprising:
   a yarn knitted into a graduated compression sock having a foot portion, an ankle portion, and a calf portion, the yarn including an elastic component and wicking fibers, the sock knitted with graduated compression from the foot portion through the calf portion, the wicking fibers configured such that, when the patient's foot is received within the foot portion, the patient's ankle is received within the ankle portion, and the patient's calf is received within the calf portion, the wicking fibers to contact a skin of at least one of the patient's foot, ankle, or calf; and
   silver nanoparticle shapes disposed on the wicking fibers, at least 30% by mass of the silver nanoparticle shapes being truncated triangular plates, triangular prisms, discs, or a combination thereof.

2. The sock of claim 1, wherein the at least 30% by mass of the silver nanoparticle shapes are truncated triangular plates with three principal axes, where a length of each of two of the three principal axes of each truncated triangular plate is more than three times greater than a length of a third principal axis of the three principal axes of each truncated triangular plate and where the length of the third principal axis is less than 50 nm.

3. The sock of claim 1, wherein the yarn is knitted to provide graduated compression of 18-24 mm Hg with compression decreasing from the foot portion through the calf portion.

4. The sock of claim 1, wherein the elastic component is disposed at a core of the yarn.

5. The sock of claim 1, wherein the elastic component is a double covered elastic yarn.

6. The sock of claim 1, wherein the wicking fibers are natural fibers selected from the group consisting of wool, merino wool, alpaca fibers and combinations thereof.

7. The sock of claim 1, wherein the silver nanoparticle shapes contribute less than 0.1% of the weight of the sock.

8. The sock of claim 1, wherein the foot portion includes a heel region and a forefoot region, the ankle portion includes a tibial crest region, and the yarn is knitted into a terry pattern in at least one of the tibial crest region, the heel region, and the forefoot region.

9. The sock of claim 1, wherein the yarn is knitted into a terry pattern configured such that, when the patient's foot is received within the foot portion and the patient's ankle is received within the ankle portion, the terry pattern is positioned to cradle the patient's medial and lateral malleoli.

\* \* \* \* \*